(12) United States Patent
Cakmak (10) Patent No.: US 9,579,507 B2
(45) Date of Patent: Feb. 28, 2017

(54) SYSTEM FOR DECREASING THE BLOOD FLOW OF A TARGETED ORGAN'S ARTERY WITH AN ELECTRICAL STIMULATION

(71) Applicant: Koc Universitesi, Istanbul (TR)

(72) Inventor: Yusuf Ozgur Cakmak, Istanbul (TR)

(73) Assignee: KOC UNIVERSITESI, Istanbul (TR)

( * ) Notice: Subject to any disclaimer, the term of this patent is extended or adjusted under 35 U.S.C. 154(b) by 0 days.

(21) Appl. No.: 14/869,782

(22) Filed: Sep. 29, 2015

(65) Prior Publication Data

US 2016/0015978 A1    Jan. 21, 2016

Related U.S. Application Data

(63) Continuation of application No. PCT/EP2013/060060, filed on May 15, 2013.

(51) Int. Cl.
*A61N 1/36* (2006.01)
*A61H 39/00* (2006.01)

(52) U.S. Cl.
CPC ....... *A61N 1/36135* (2013.01); *A61H 39/002* (2013.01); *A61N 1/3606* (2013.01); *A61N 1/36014* (2013.01); *A61H 2201/0214* (2013.01); *A61H 2201/0285* (2013.01); *A61H 2201/501* (2013.01); *A61H 2201/5043* (2013.01); *A61H 2201/5046* (2013.01); *A61H 2201/5097* (2013.01); *A61H 2230/065* (2013.01); *A61H 2230/305* (2013.01)

(58) Field of Classification Search
CPC ... A61B 5/4836; A61B 5/743; A61B 5/02007; A61B 5/7271; A61B 5/0205; A61B 5/026; A61B 5/7475; A61B 5/02028; A61B 5/04; A61B 5/486; A61B 5/7485; A61B 5/02042; A61B 5/024; A61B 7/04; A61B 2560/04; A61B 2560/02; A61B 2560/06; A61B 5/00; A61B 5/0082; A61B 5/02; A61B 5/145; A61B 5/7445; A61B 5/7465; A61B 6/463; A61N 1/36; A61N 1/205; A61N 1/36185; A61N 1/375; A61N 1/0472; A61N 1/08; A61N 1/36125; A61N 1/36132; G06F 19/3418; G06F 19/345; G06F 19/321; G06F 19/3406; G06F 19/3481; G08B 21/0453; G06T 7/0012

See application file for complete search history.

(56) References Cited

U.S. PATENT DOCUMENTS

2002/0138116 A1    9/2002    Bertolucci
2003/0114900 A1    6/2003    Mellen
(Continued)

FOREIGN PATENT DOCUMENTS

WO    WO 01/52931 A1    7/2001
WO    WO 2010/088914 A1    8/2010
WO    WO 2012/058289 A2    5/2012

OTHER PUBLICATIONS

International Search Report and Written Opinion of the International Searching Authority, dated Sep. 3, 2013, pp. 1-9, issued in International Application No. PCT/EP2013/060060, European Patent Office, Rijswijk, The Netherlands.

*Primary Examiner* — Deborah Malamud
(74) *Attorney, Agent, or Firm* — Brinks Gilson & Lione (57) ABSTRACT

A system for decreasing the blood flow of a targeted organ in case of bleeding or a medical requirement includes an integrated electrostimulator and a subsystem.

10 Claims, 6 Drawing Sheets

(56) References Cited

U.S. PATENT DOCUMENTS

2004/0230256 A1  11/2004  Lin-Hendel
2007/0270917 A1  11/2007  Nachum
2011/0263950 A1* 10/2011  Larson ................... A61B 5/024
                                              600/301

* cited by examiner

Transcutaneous/Percutaneous Electrode Placement in according to the target organ or organs and desired level of bloodflow decrease as shown in the displaying unit Electrostimulation with 60-90 hertz (0.1-300 μs pulse duration-Bipolar) and intensity increased just below the individual's pain threshold Blood flow decrease within 5 min in the target organ or organ's artery

SYSTEM FOR DECREASING THE BLOOD FLOW OF A TARGETED ORGAN'S ARTERY WITH AN ELECTRICAL STIMULATION

RELATED APPLICATIONS

The present patent document is a continuation of PCT Application Serial No. PCT/EP2013/060060, filed May 15, 2013, which is hereby incorporated by reference.

FIELD OF INVENTION

The present invention relates to a system for diagnosing the severity of internal bleeding in a patient, which outputs data displayed for skin electrostimulation map and guides skin placements of the system integrated electrodes which apply electrostimulation to decrease blood flow into an organ or organs.

BACKGROUND

Current products to decrease the internal organ bleeding include externally applied foams, clothes or devices that need surgical implantation. Further, the products are not organ specific, and further, the devices that are placed into or around the vessels with surgical applications or these devices use mechanical compressions, chemical reactions or local muscle contraction methods.

SUMMARY

The present disclosure relates to a system to decrease the blood flow of a targeted organ in case of bleeding or a medical requirement, characterized in that the system comprises an integrated electrostimulator, which comprises electrodes to be placed to the skin of a patient, and a subsystem which comprises a processor, at least one first input means (e.g., sensor input device) and at least one second input means (e.g., user interface device). The first input means comprises a blood pressure measurement and pulse detector unit and the second input means is a device enabling the user to enter the wound or bleeding area information into the system. The processor of the subsystem can be executed according to an algorithm embedded or stored in memory, such as in the subsystem, to determine where the electrodes are placed according to the analyzed blood pressure measurement, pulse, and inputted wound or bleeding area information, and the processor is further executable to cause display of a location where the electrodes are placed on the patient through at least a skin map.

An interesting aspect of system is the capability to overcome internal bleedings with the aid of an organ based targeting system without a need for a surgery, intravascular applications or a medical professional, and to provide an extended time for homeostasis to allow medical professional's help and/or surgical applications.

THE COMPONENTS IN SAID FIGURES ARE INDIVIDUALLY REFERENCED AS FOLLOWS:

Display unit (10)
Electrodes (11)
Wound or bleeding area (12)
Blood pressure measurement and pulse detector unit (13)
Wireless communication equipment (14)
L5 dermatome (a)
L4-S2 dermatome (b)
T12 dermatome (c)
T10 dermatome (d)

DETAILED DESCRIPTION

The disclosure relates to a system comprising an integrated specific electrostimulator to decrease the blood flow to a targeted internal organ in case of an internal bleeding or a medical condition requiring a surgery. The system further comprises a subsystem which comprises a processor, at least one first input means and at least one second input means. The first input means comprises a blood pressure measurement and pulse detector unit and the second input means is a user input device enabling the user to enter the wound or bleeding area information into the system. The processor included in the subsystem determines where the electrodes are placed according to analyzed blood pressure, pulse and inputted wound or bleeding area information according to an algorithm stored in a memory included in the subsystem, the processor of the subsystem further executable to display where the electrodes are placed on the patient through at least a skin map.

Figure 2:
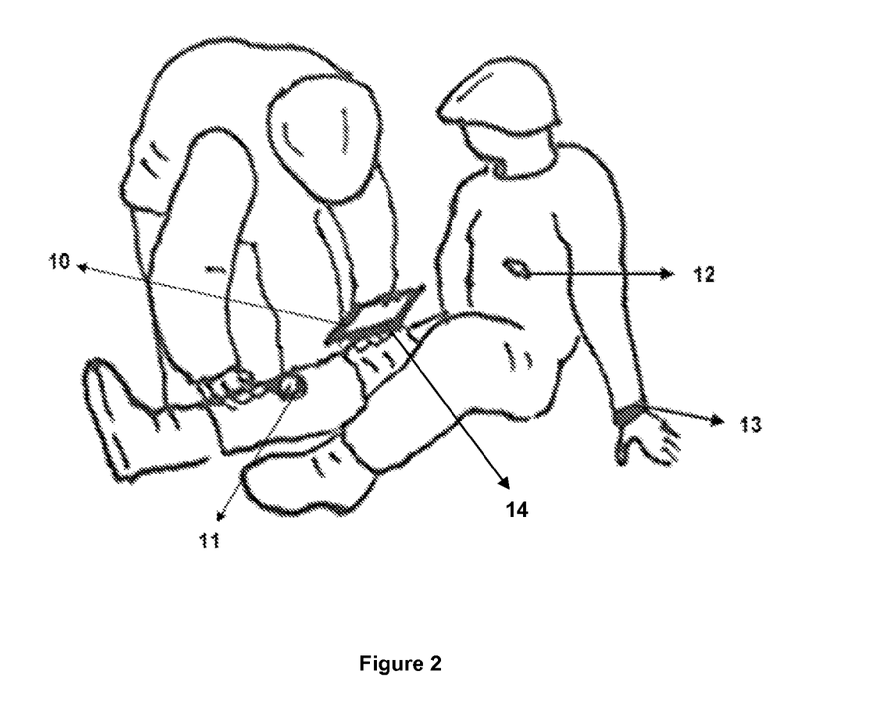
FIG. 2 shows an illustration of an example of the system's components application.

Another example relates to a system used for decreasing the blood flow of a targeted internal organ's artery with an electrical stimulation (FIG. 2). The system operation comprises the following steps:

Transcutaneous/Percutaneous electrode (11) placement according to the target organ or organs and desired level of blood flow decrease as shown in the display unit (10), Electrostimulation with 60-90 hertz (0.1-300 µs (microsecond) pulse duration—bipolar) and intensity increased just below the individual's pain threshold, and Blood flow decrease within 5 min in the target organ or organ's artery.

Another example is related to a handheld system which uses specific combinations of the electrical stimulation (percutaneous and/or transcutaneous) and skin dermatomal (a skin area that is supplied by a nerve) zones to decrease the blood flow of a desired internal organ. Further, said system lets the user calibrate the level of the decreases in blood flow of the desired organ's artery between 20% to 44% percent with specific placement of combinations of the electrodes' over the different skin dermatomes in 3-5 minutes.

In addition, the system comprises a current limiter circuitry that provides a means for high current blocking for currents exceeding 15 mA to avoid skin burning and preferably comprises thermoelectric coolers to cool the skin around the electrodes and avoid burning. Such functionality is useful, for example, when using higher currents to avoid burning of the skin. In the case of using currents exceeding 15 mA, the high current limiter can be switched off. Thermoelectric coolers can be also used at current levels below 15 mA.

The system further comprises an integrated visual and acoustic alarm system for the user to manage the internal bleeding of more than one individual. This would be important, if for example more than one individual is wounded and the same doctor has to care for all of the patients. The system can further comprise communication means such as wireless communication equipment (14) to inform the doctor or first aid personal. The communication means sends attributed data, which contains blood pressure and heart beat data, in a coded form enabling error detection and error correction and making the communication less vulnerable to noise. Such coding techniques are known in the art.

Figure 1:
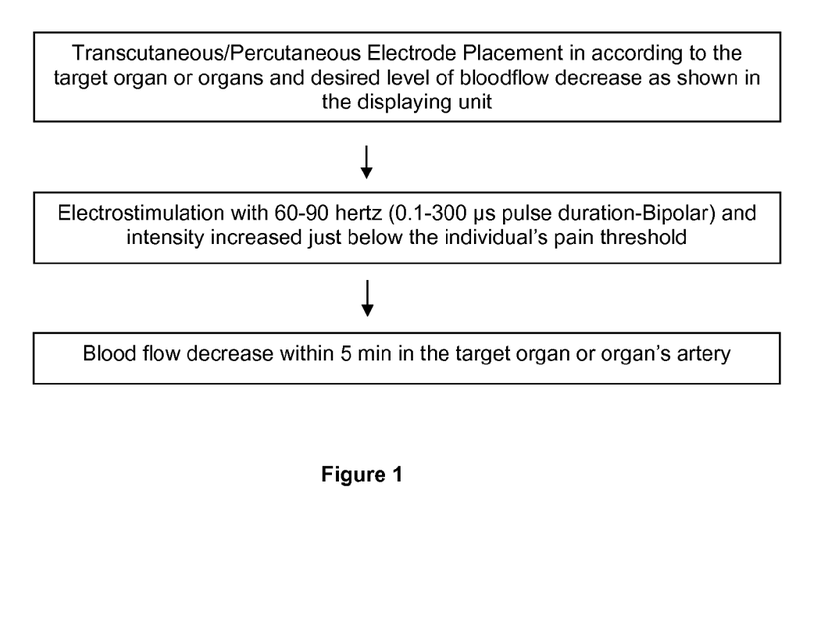
FIG. 1 is a flowchart of an example stimulator application and electrode placement.

The processor can execute the algorithm included in the subsystem for: monitoring the heart rate and blood pressure measured, i.e., separately or in combination, wherein the measurements can be taken from the fingers, arm and wrist of a patient by the blood pressure measurement and pulse detector unit (13), and interpretation of the data reflected as an electrode placement map on the display unit (10) with specific software (FIG. 1).

The system can provide a computer-aided diagnosis system comprising a subsystem wherein the subsystem has the following components:
  first input means, or one or more units, for blood pressure and pulse data of an individual with an internal organ bleeding,
  memory or means for storing a plurality of computer-aided diagnosis algorithms executable by a processor and a skin map for electrode placement,
  means for selecting, such as selection using a user interface, based on the inputted blood pressure and pulse data, the power of blood decreasing level in the targeted organ/organs,
a processor executing an optimum computer-aided diagnosis algorithm stored in memory to provide a skin map of the electrode placement, and an integrated visual and acoustic alarm system
  means to analyze, and display data, i.e., a microprocessor based system with a display,
  means for guiding electrode placement and the number of electrodes (11) to be used in related to the severity of the internal organ bleeding, wherein the means for guiding is preferably a display unit (10).
The computer-aided diagnosis system further comprises:
a stimulation unit, which comprises an integrated specific electrostimulator and electrodes (11), and
a connection network to provide electrical power connections and signal connections to all units.

The electrostimulator along with the electrodes (11), display unit (10) and blood pressure measurement and pulse detector unit (13) can also be used solely.

The system can further comprise second input means, such as a user interface device. Second input means can be embedded in a means for guiding, wherein the means for guiding is preferably a display unit (10). Said display unit can be a keyboard or a touch screen display, enabling the user, who can be either a person providing a first aid or even the wounded person himself, to enter the wound or bleeding area information into the system. This information is the location of the wound or bleeding area on the patient's body.

In case of a touch screen display being used as a user interface means for guiding, second input means can be embedded in the means for guiding, so that the display unit accepts input as well as guides the user where to put the electrodes (11). In such case the user can also pinpoint the location of the wound or bleeding area on a body by drawing on a picture appearing on the display.

The skin map for electrode placement contains the location information, where to put the electrodes of the integrated specific electrostimulator, according to the location of the wound or bleeding area and according to the attributed data.

Underlying Mechanism of Decreasing the Blood Flow and an Organ Specific Skin Map:

Segmental receptive field of a multireceptive neurone in the spinal cord is located on the skin and is made up of an excitatory and an inhibitory field. The receptive field very often includes a visceral component and a peculiar convergence of information onto a single neuron occurs [D. Le Bars/Brain Research Reviews 40(2002)29-44]. Sympathetic nerve fibers of the peripheric nerve system are the main target of the internal organ's blood flow decreasing effects that is achieved by high frequency electrostimulation. The stimulation frequency can be between 60 Hz and 90 Hz, preferably at 80 Hz. The pulse duration can be between 0.1-300 μs (microseconds).

Percutaneous nerve stimulation or electroacupuncture (EA) shows a very selective action in increasing or decreasing blood flow of a target organ, when appropriate nerve and stimulation frequency combinations are used (Cakmak Y O, Akpinar I N, Ekinci G, Bekiroglu N. Point- and frequency-specific response of the testicular artery to abdominal electroacupuncture in humans. Fertil Steril 2008;90:1732-8. Ho M, Huang L C, Chang Y Y, Chen H Y, Chang W C, Yang T C, et al. Electroacupuncture reduces uterine artery blood flow impedance in infertile women. Taiwan J Obstet Gynecol 2009; 48:148-51. Stener-Victorin E, Kobayashi R, Watanabe O, Lundeberg T, Kurosawa M. Effect of electroacupuncture stimulation of different frequencies and intensities on ovarian blood flow in anaesthetized rats with steroid-induced polycystic ovaries. Reprod Biol Endocrinol 2004; 26:2-16.). It has been previously demonstrated (Cakmak Y O, Akpinar I N, Ekinci G, Bekiroglu N. Point- and frequency-specific response of the testicular artery to abdominal electroacupuncture in humans. Fertil Steril 2008;9 0:1732-8.) that blood flow can be increased in the testicular artery of humans with EA by using a specific combination of stimulation frequency and a dermatome, using the effective frequencies that have been proven to increase blood flow in rats by revealing the arterial diameter and area changes in addition to blood flow for the first time in the literature. In the same research, it was also demonstrated that closely neighboring dermatomes (T10-T12) do not have the same ability to affect the same organ in means of blood flow.

Ovarian blood flow-decreasing parameters of electrostimulation in rats had been described (Stener-Victorin E, Kobayashi R, Watanabe O, Lundeberg T, Kurosawa M). Effect of electroacupuncture stimulation of different frequencies and intensities on ovarian blood flow in anaesthetized rats with steroid-induced polycystic ovaries. (Reprod Biol Endocrinol 2004; 26:2-16.). For the first time, in humans, it was demonstrated the optimal blood flow decreasing parameters and dermatome combinations of electrostimulation for human internal organ arteries as the uterine artery in which we decreased the extreme bleeding with a fibroma origin. It has been demonstrated that only high-frequency EA can decrease ovarian blood flow in rats; on the other hand, the neuroanatomical pathways that aid such a function consider central effects in addition to segmental innervation because the ovarian blood flow responses to high frequency EA stimulation were also investigated after severance of the ovarian sympathetic nerves in rats (Stener-Victorin E, Kobayashi R, Watanabe O, Lundeberg T, Kurosawa M). Effect of electroacupuncture stimulation of different frequencies and intensities on ovarian blood flow in anaesthetized rats with steroid-induced polycystic ovaries. (Reprod Biol Endocrinol 2004; 26:2-16.).

Innervation territories of the single sympathetic C fibers in human skin has different accumulations in different skin zones (J Neurophysiol. 1998 April; 79(4):1653 60. Innervation territories of single sympathetic C fibers in human skin. Schmelz M, Schmidt R, Bickel A, Torebjörk H E, Handwerker H O, Neurophysiol Clin. 2003 December; 33(6):315-24.Trigeminal responses to laser stimuli. Romaniello A, Iannetti G D, Truini A, Cruccu G).

Figure 3:
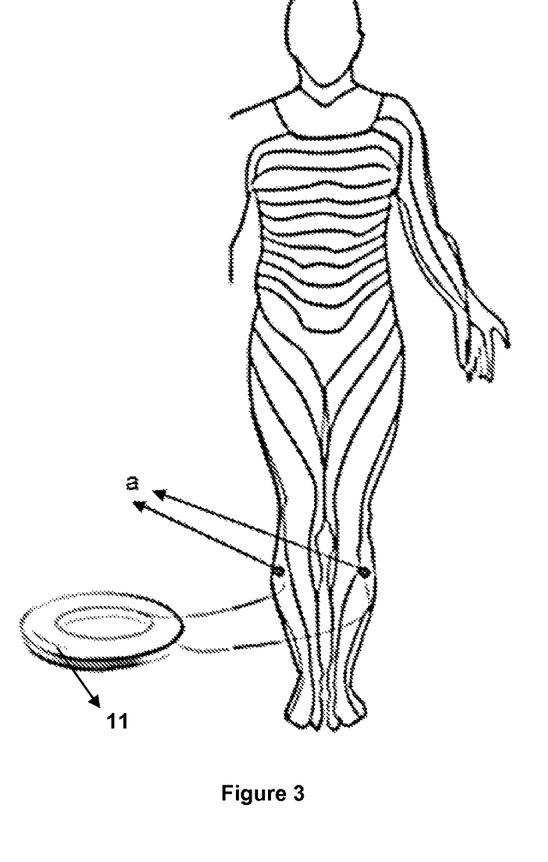
FIG. 3 shows an example of bilateral placement of the two electrodes on placement skin maps to achieve a 20% blood flow decrease to liver, stomach, kidney, spleen and proximal large intestines.
Figure 4:
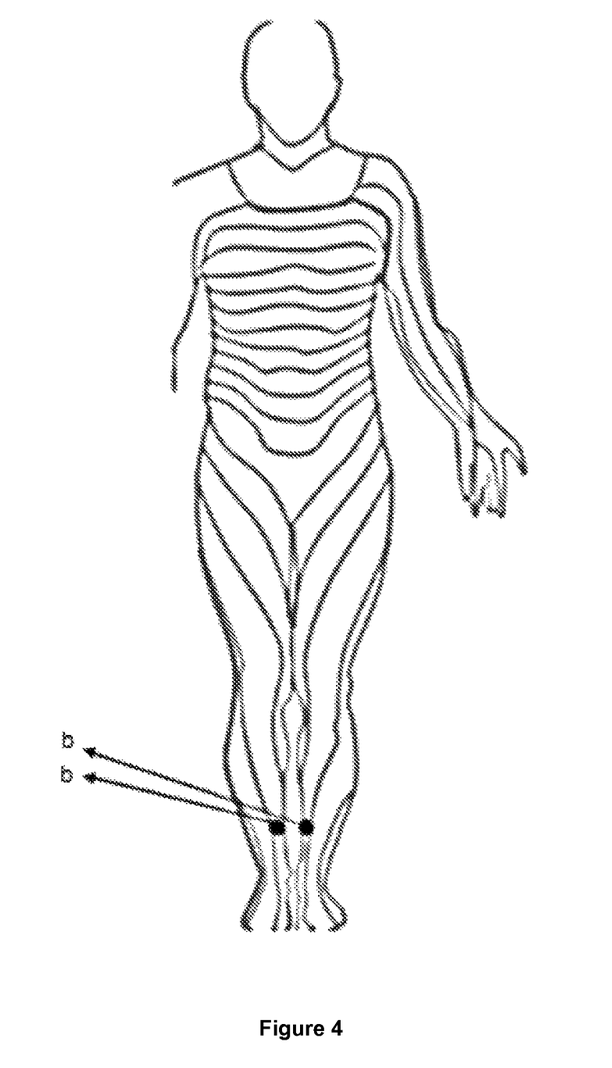
FIG. 4 shows other an example of bilateral placement of the two electrodes on placement skin maps to achieve a 20% blood flow decrease to distal large intestine, testicles (gonads), prostate gland and bladder.
Figure 5:
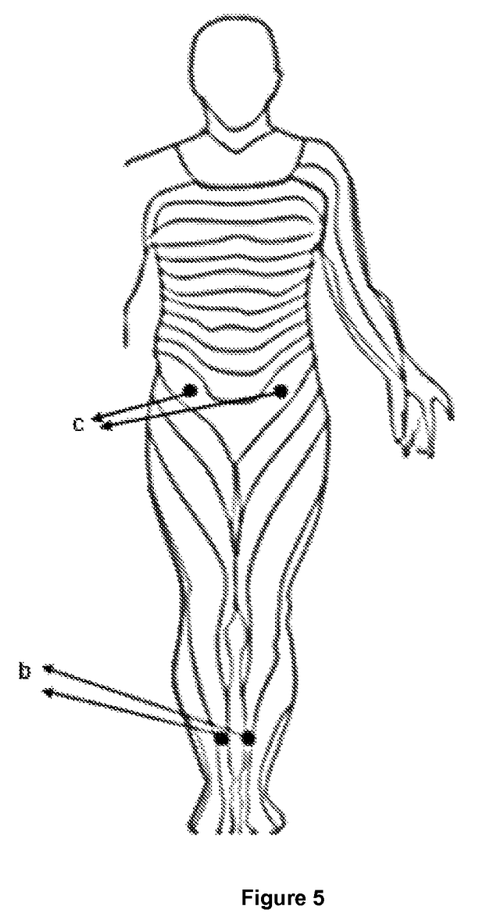
FIG. 5 shows an example of bilateral placement of the four electrodes on placement skin maps to achieve a 40% blood flow decrease to distal large intestine, testicles (gonads), prostate gland and bladder.
Figure 6:
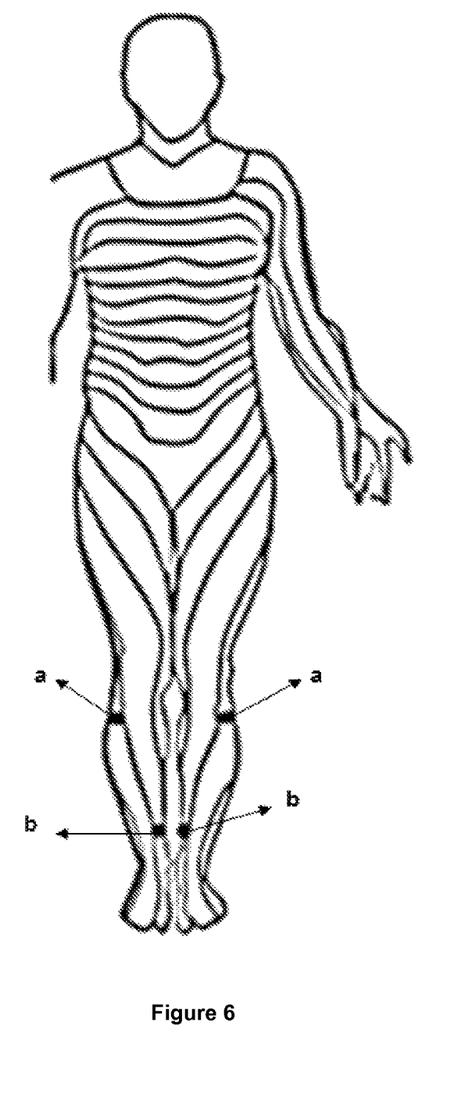
FIG. 6 shows another example of bilateral placement of the four electrodes on placement skin maps to achieve a 40% blood flow decrease to all abdominal organs.
Figure 7:
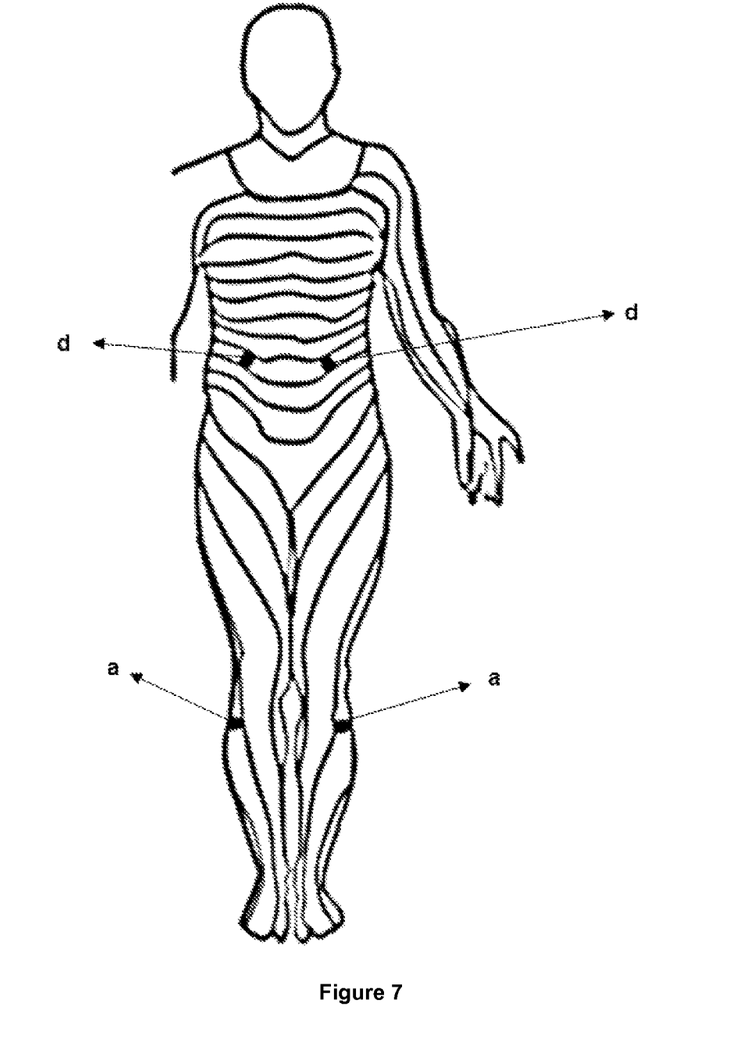
FIG. 7 shows another example of bilateral placement of the four electrodes placement skin maps to achieve a 40% blood flow decrease to the liver, stomach, spleen and proximal large intestine.

In conclusion, to decrease the blood flow in a specific internal organ an optimal combination of stimulation zone of a dermatome and frequency for that specific organ (or organs supplied by the same arterial origin) is needed. Bilateral Placement of the 2 electrodes (11) over the L5 dermatome (a) common peroneal nerve territory, anterior to the head of fibular bone impression results in about a 20% decrease of the blood flow to Liver, Stomach, Kidney, Spleen and Proximal Large intestines within 5 minutes (FIG. 3). Bilateral placement of the 2 electrodes (11) over the L4-S2 dermatome (b)—saphenous nerve territory, 5-6 cm above the medial malleolus results in about a 20% decrease of the blood flow to Distal large intestine, testicles (gonads), Prostate gland and Bladder within 5 min (FIG. 4). To achieve 40% blood flow decrease for a specific organ, 4 electrode (11) placements can be used. Bilateral Placement of the 4 electrodes (11) over the L4-S2 dermatomes (b)—saphenous nerve territory, 5-6 cm above the medial malleolus and the T12 dermatome (c) results in about a 40% decrease of the blood flow to distal large intestine, testicles (gonads), Prostate gland and Bladder within 5 min (FIG. 5). Bilateral Placement of the 4 electrodes (11) over the L4-S2 dermatomes (b)—saphenous nerve territory, 5-6 cm above the medial malleolus and the L5 dermatome (a)—common peroneal nerve territory-anterior to the head of fibular bone impression or (over the T10 and T12) results in about a 40% decrease of the blood flow to all abdominal organs (FIG. 6). Bilateral Placement of the 4 electrodes (11) over the L5 dermatome (a)—common peroneal nerve territory-anterior to the head of fibular bone impression and the T10 dermatome (d) decrease blood flow to the Liver, Stomach, Spleen and Proximal Large intestines (FIG. 7).

This can be more fully understood from the detailed description when taken in conjunction with the accompanying FIGS. 3 to 7.

What is claimed is:

1. A system to decrease the blood flow of a targeted organ in case of bleeding or a medical condition of a patient, the system comprising:
    an integrated electrostimulator comprising an electrode configured to be placed to the skin of the patient, the electrode configured to apply electrostimulation to decrease blood flow, and
    a subsystem comprising:
        a processor included in the subsystem,
        a sensor input device comprising a blood pressure measurement and a pulse detector unit, and
        a user interface device to enable a user to enter wound area or bleeding area information into the system,
        the processor executed to determine where application of electrostimulation by the electrode decreases blood flow according to analyzed blood pressure, pulse and inputted wound area or bleeding area information, and the processor further executed to display a location on the skin of the patient where the electrode should be placed through at least a skin map.

2. The system according to claim 1, the user interface comprises a selection, based on the inputted blood pressure and pulse data, of a power of blood decreasing level in the targeted organ.

3. The system according to claim 2, comprising an integrated visual and acoustic alarm system.

4. The system according to claim 1, further comprising a high current blocker device configured to block currents at the electrode exceeding 15 mA to avoid skin burning.

5. The system according to claim 4, further comprising thermoelectric coolers to cool the skin around the electrode.

6. The system according claim 1, the user interface device comprises a display unit.

7. The system according to claim 6, the display unit comprises a touch screen display.

8. The system according to claim 6, where each of: the integrated electrostimulator, the display unit and the blood pressure measurement and pulse detector unit are individually operable.

9. The system according to claim 1, the integrated electrostimulator is configured to apply a bipolar electrical signal with stimulation frequency between 60 Hz and 90 Hz and pulse duration between 0.1-300 microseconds.

10. The system according to claim 1, the integrated electrostimulator is configured to apply a bipolar electrical signal with stimulation frequency at 80 Hz and pulse duration between 0.1-300 microseconds.

* * * * *